(12) United States Patent
Geller et al.

(10) Patent No.: US 7,914,531 B1
(45) Date of Patent: Mar. 29, 2011

(54) BONE FIXATION SYSTEM AND METHODS

(76) Inventors: David S. Geller, New York, NY (US); Dan Zlotolow, Baltimore, MD (US)

(*) Notice: Subject to any disclaimer, the term of this patent is extended or adjusted under 35 U.S.C. 154(b) by 538 days.

(21) Appl. No.: 11/244,407

(22) Filed: Oct. 6, 2005

Related U.S. Application Data

(60) Provisional application No. 60/615,965, filed on Oct. 6, 2004, provisional application No. 60/695,857, filed on Jul. 5, 2005.

(51) Int. Cl.
*A61B 17/58* (2006.01)
(52) U.S. Cl. .......................... 606/60; 606/278
(58) Field of Classification Search ............ 606/54, 606/55, 57–60, 264, 266, 267, 270
See application file for complete search history.

(56) References Cited

U.S. PATENT DOCUMENTS

| | | | | |
|---|---|---|---|---|
| 2,372,866 A * | 4/1945 | Tofflemire | ............... | 606/54 |
| 2,501,978 A * | 3/1950 | Wichman | ............... | 606/71 |
| 4,289,124 A * | 9/1981 | Zickel | ............... | 606/60 |
| 4,628,923 A * | 12/1986 | Medoff | ............... | 606/65 |
| 5,474,551 A * | 12/1995 | Finn et al. | ............... | 606/264 |
| 5,476,463 A * | 12/1995 | Boachie-Adjei et al. | ..... | 606/264 |
| 5,527,310 A * | 6/1996 | Cole et al. | ............... | 606/60 |
| 5,630,817 A * | 5/1997 | Rokegem et al. | ............ | 606/269 |
| 6,056,748 A * | 5/2000 | Weiner | ............... | 606/55 |
| 6,585,736 B2 | 7/2003 | Hajianpour | | |
| 6,660,009 B1 | 12/2003 | Azar | | |
| 6,682,561 B2 | 1/2004 | Songer et al. | | |
| 6,692,496 B1 | 2/2004 | Wardlaw | | |
| 6,716,212 B1 | 4/2004 | Pickens | | |
| 7,255,701 B2 * | 8/2007 | Allen et al. | ............... | 606/74 |
| 2003/0114852 A1 | 6/2003 | Biedermann et al. | | |

* cited by examiner

*Primary Examiner* — Thomas C Barrett
*Assistant Examiner* — Nicholas Woodall
(74) *Attorney, Agent, or Firm* — Rothwell, Figg, Ernst & Manbeck pc

(57) ABSTRACT

An internal system and method for fixating an appendicular bone fracture in an individual. A plurality of fixating screws, each of which is adapted for placement in the bone at an anatomically favorable position, and at least one of which is adapted to provide interfragmentary reduction of the bone fracture are connectable to a rigid rod to provide bone fixation. A fracture positioning clamp for holding a reduced fracture in place until application of a fixation system.

1 Claim, 16 Drawing Sheets

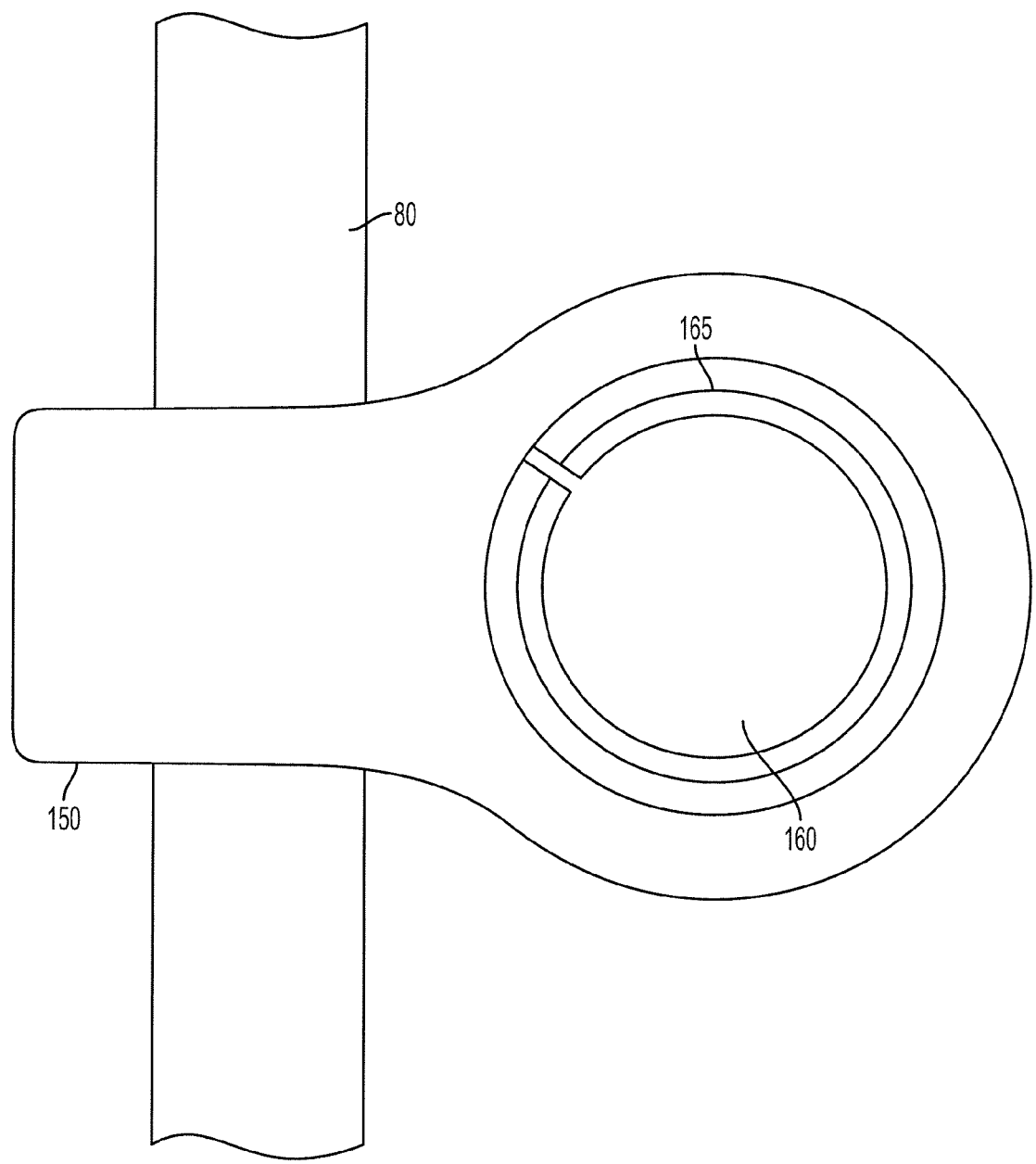

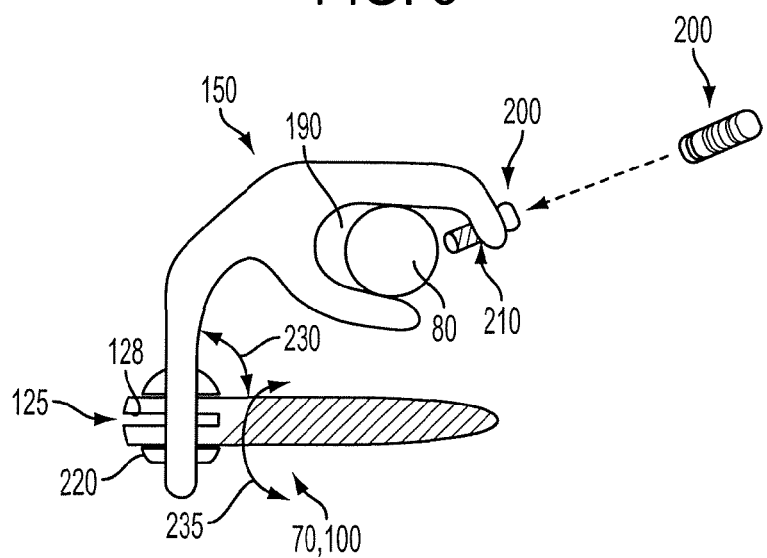

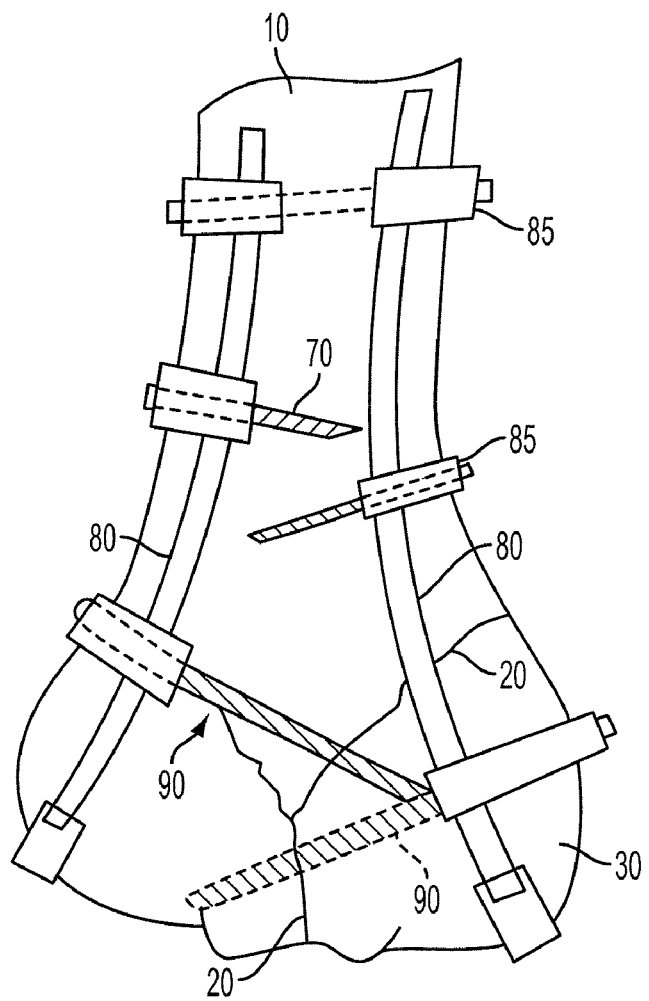

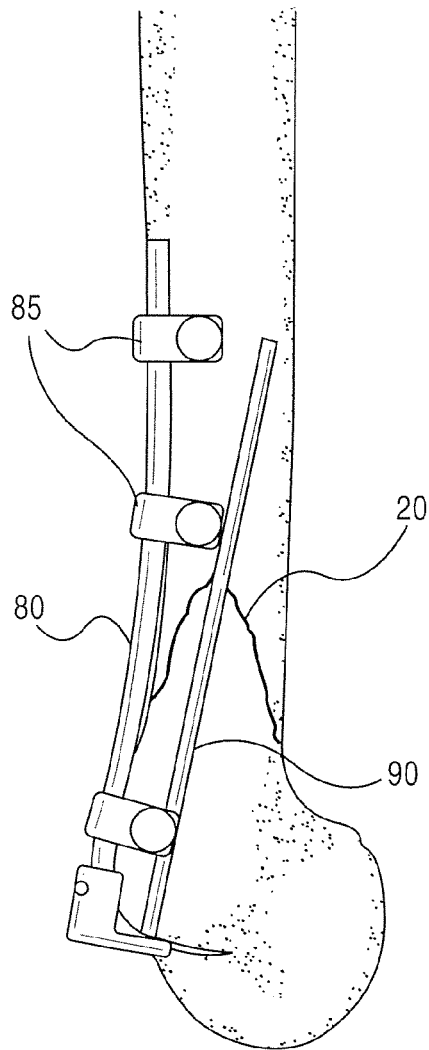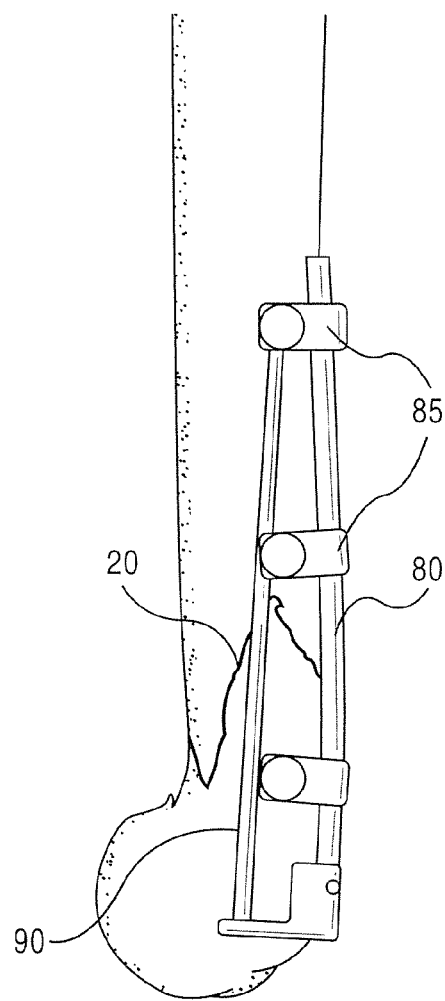
FIG. 10A                    FIG. 10B

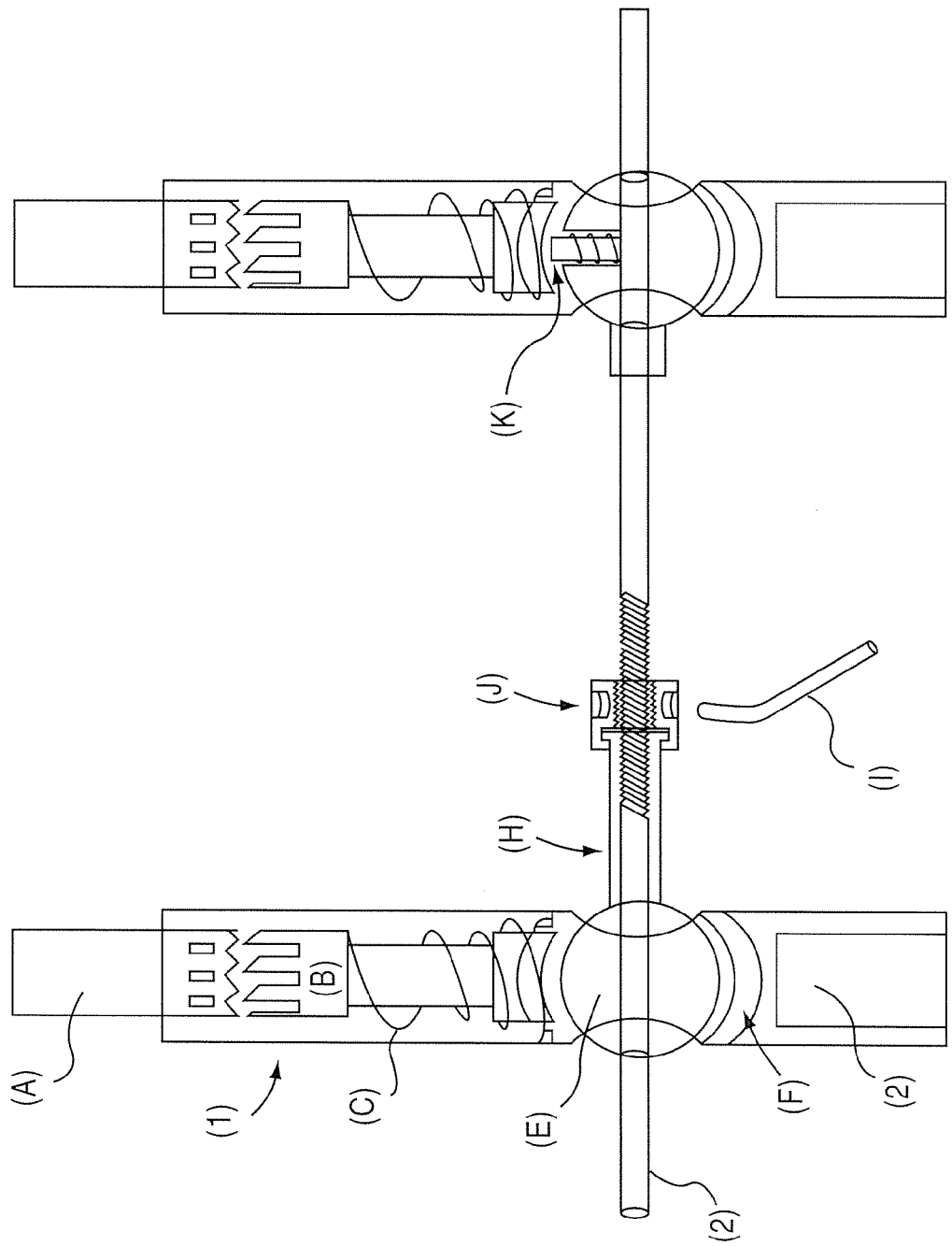

BONE FIXATION SYSTEM AND METHODS

This application claims benefit of U.S. Provisional Patent Application No. 60/615,965, filed Oct. 6, 2004 and U.S. Provisional Patent Application No. 60/695,857, filed Jul. 5, 2005, both of which are hereby incorporated in their entireties into the present application.

FIELD OF THE INVENTION

The present invention relates generally to medical devices, and more particularly to bone fracture fixation systems.

BACKGROUND OF THE INVENTION

All United States Patents referred to herein are hereby incorporated by reference in their entireties. In the case of conflict, the present specification, including definitions, will control.

Numerous methods and devices are known and available for stabilizing and fixating bone fractures in various bone types in an individual. These include both external and internal fixation systems. For example, U.S. Pat. No. 6,682,561 refers to an implantable spinal, vertebral replacement device that includes a tubular cage and a series of plates and screws. Other spinal stabilization systems used in posterior spinal fusions also involve plate and screw constructs. Such systems are limited in their effectiveness in that screw placement depends on the locations of the plate holes. As a result, screws are placed in sub-optimal locations and at sub-optimal angles that could threaten neurovascular injury and compromise fracture fixation. Recent spinal stabilization techniques have employed modular rod and screw systems that allow more flexibility in screw placement, by permitting the screws to be placed first, after which they are affixed to a common rod.

Various other systems exist for fixating bones. U.S. Pat. No. 6,660,009 refers to nails and a nail insertion device used in the fixation of distal radial fractures. U.S. Pat. No. 6,692,496 refers to an internal fixation device that employs the axial insertion and anchoring of elongate members into long bones to treat fractures.

U.S. Pat. No. 6,585,736 refers to external fixation of a fractured radius using a variety of components, including rods, pins, clamps, and sliding plates. U.S. Pat. No. 6,716,212 refers to an external rod and clamp construct for use in immobilizing or stabilizing unexposed long bone fractures in patients who are unable to undergo definitive fixation. The system involves percutaneous pins placed through stab incisions, which pins are then fastened to external rods.

The fixation of certain fractures, such as comminuted intra-articular fractures in the appendicular skeleton, is not adequately addressed in the art. Important considerations in fixating such fractures include the need for proper anatomic alignment and rigid fixation. Current fixation techniques typically rely upon the use of plates and screws once an anatomic reduction has been achieved. These plate systems do not allow for flexibility in screw placement, which is necessary for achieving optimal interfragmentary fixation. Often, screws are used outside of the plate construct in order to augment fixation.

FIG. 1 illustrates a typical internal fixation device used in the art, which exhibits the above inadequacies. In this figure, the device is employed in an effort to fixate fractures 20 in a bone 10. The fractures have resulted in several fragments 30 being present. This device involves one or more plates 40 which have within them a series of holes 50 for securing the plates to the bone using screws 60. As can be seen from the figure, the placement of the screws is entirely dictated by the locations of the holes in the plates. These limitations in screw placement, including the angle in which the screw can be inserted, frequently result in anatomically inadequate or inappropriate placement of screws, which can lead to improper fixation, limited effectiveness in healing, limited range of motion, and damage or disruption to nerves or vessels.

Recent advances in plate fixation systems have incorporated locking screw designs in which the screw head threads into the plate, providing a fixed-angle screw-plate construct. This concept, adapted from anterior spinal instrumentation systems, has increased the rigidity of the overall construct and the pull-put strength of the screws, but at the cost of further limiting angular screw positioning.

There is thus a need in the art for a system and method that mitigates or eliminates the above disadvantages and inadequacies seen in the art, while maximizing the advantages of rigidity via fixed angle devices. In particular, there is a need for a system and method for providing a strong, rigid bone fixation in a manner that is anatomically appropriate for the individual.

SUMMARY OF INVENTION

To overcome the problems associated with previous bone fixation systems, the present invention provides systems and methods for the stabilization or fixation of bone or bony fragments in the appendicular skeleton of an individual. In an aspect, the invention provides a modular rod and screw system comprising a series of screws placed in optimal anatomic position, to which a rod or rods are attached using multiple connectors and fasteners. This system allows the clinician a greater degree of flexibility and choice of screw position than is afforded by conventional systems, particularly plate systems as described above.

In a preferred embodiment, the invention provides an internal system for fixating an appendicular bone fracture in an individual. The system comprises a plurality of fixating screws, each adapted for placement in the bone at an anatomically favorable position, wherein at least one of the fixating screws is adapted to provide interfragmentary reduction of the bone fracture and at least one rigid rod attachable to the fixating screws to provide fixation of the bone fracture.

In an aspect, the invention also provides a system for fixating an appendicular bone fracture in an individual, the system comprising a plurality of fixating screws, each adapted for placement in the bone at an anatomically favorable position, and at least one rigid rod attachable to the plurality of screws by a plurality of connecting devices.

The invention also provides a fracture positioning clamp that serves to temporarily hold a fracture in place after reduction so that screws, such as lag screws, can be appropriately placed in an anatomically favorable position to secure the reduced fracture in place until a rigid fixation system is applied. The screws may serve as the fixating screws of a fixation system described herein, or of any other appropriate fixation system that would benefit from the unique advantages provided by the fracture positioning clamp. Alternatively, additional fixating screws may be applied as appropriate, as described herein in connection with fixation systems.

In an embodiment, the fracture positioning clamp comprises a plurality (preferably two) of holding devices, each of which comprises a substantially cylindrical housing within which is located a mechanism for imparting a direct or indirect depressional and/or rotational force upon a partially threaded rod. The depressional and/or rotational force causes each holding device to securely engage the partially threaded rod, thereby locking the holding devices in position relative to each other and thereby holding the reduced fracture in place until the fracture is further secured (such as with a lag screw) and a fixation system applied.

The invention further provides methods of reducing and fixating bone fractures using the systems and clamps described herein.

BRIEF DESCRIPTION OF THE DRAWINGS

FIGS. 8 and 8A illustrate a relationship between a clamp, fixating screw, and rod in accordance with an embodiment of the invention.

FIGS. 10-10B are schematics depicting fixation systems in accordance with the invention.

FIG. 11 depicts a fracture positioning clamp in accordance with the invention.

DETAILED DESCRIPTION OF THE INVENTION

Figure 1:
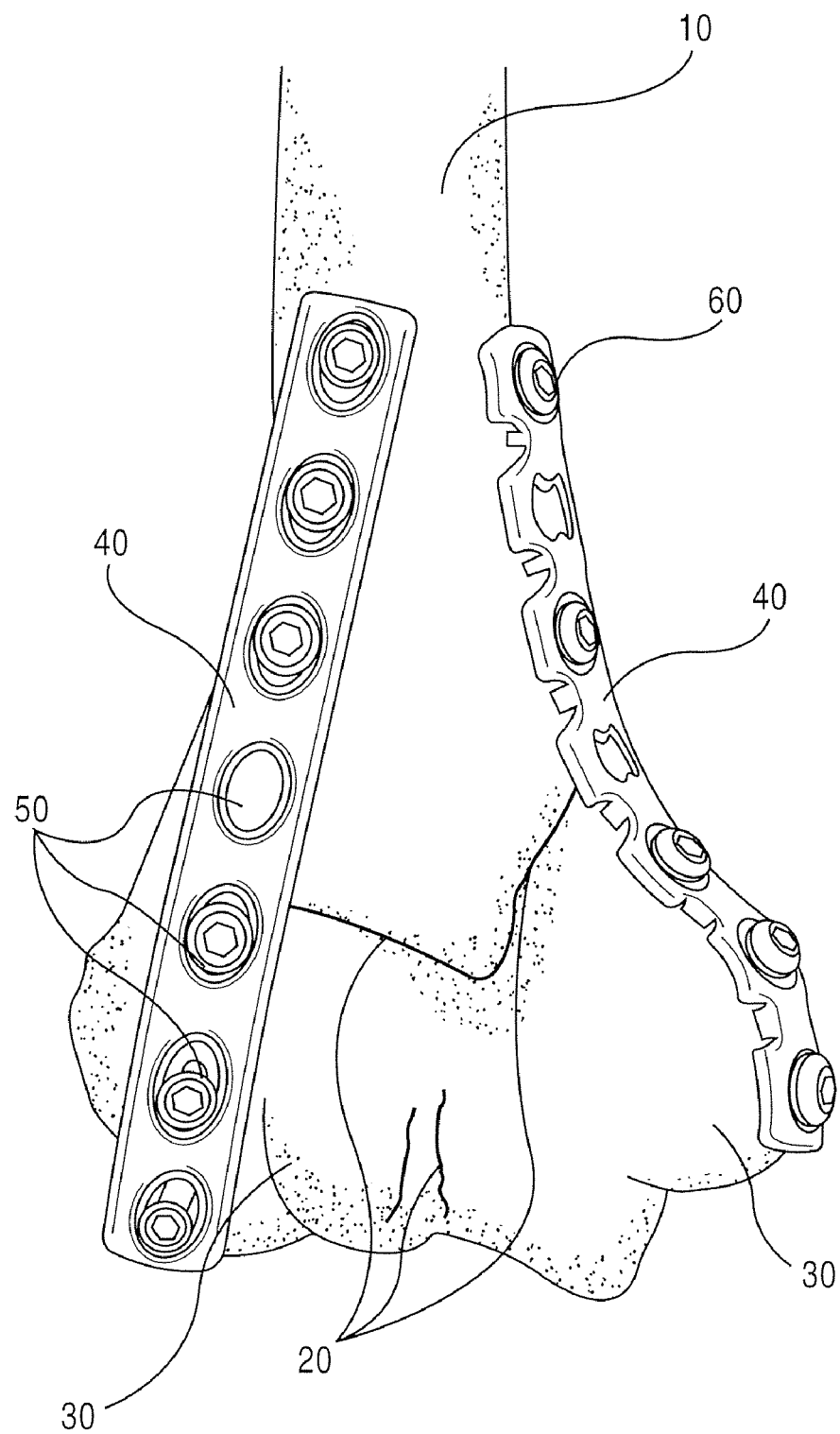
FIG. 1 is a photograph of a conventional prior art plate and screw system for fixating bone fractures.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

As used herein, an internal fixation system relates to a system that allows for soft tissue closure.

As used herein, an "anatomically favorable position" refers to any position chosen for screw placement that is deemed medically or anatomically beneficial to achieve proper fixation while minimizing potential for damage to bone, nerves, vessels, or other tissue.

As used herein, "interfragmentary reduction" and "interfragmentary compression" refer to the bringing together of two or more bone fragments either positionally or in lag fashion.

An "intra-articular" fracture is a fracture occurring at an articulated interface between bones.

As used herein, a "rod" refers to any rod or rod-plate combination construct which can be used to link or reversibly attach the various screws and connectors in accordance with the invention. The rod can be sized and shaped as appropriate to achieve the results described herein. Similarly, a "partially threaded rod" refers to a rod described as above, which contains threads on at least a portion of its surface to engage other components of the fracture positioning clamp as described herein.

The present invention provides an internal system for fixating an appendicular bone fracture in an individual. The system comprises a plurality of fixating screws, each adapted for placement in the bone at an anatomically favorable position, wherein at least one of the fixating screws is adapted to provide interfragmentary reduction of the bone fracture, and at least one rigid rod attachable to the fixating screws to provide fixation of the bone fracture. The invention further provides methods of fixating bones using such systems.

The present invention overcomes the limitations of screw placement dictated by plate fixation and allows for optimal interfragmentary screw fixation, which ultimately is locked into the overall construct. This can be accomplished in accordance with methods of the present invention by placing all fixating screws in the desired locations as appropriate according to the individual fracture pattern.

In a preferred embodiment, once interfragmentary screw fixation is accomplished, low-profile clamps can be placed over each screw head. Locking screws can then be provisionally placed into the screw head, loosely holding the clamps in place. A rigid rod, which may be contoured or otherwise appropriately shaped, is fitted into the clamps and locked in place using fastener screws. The screws are finally locked into the clamps by tightening the locking screws. The tightening screws thread into the screw head and force it to expand, locking the entire construct.

Referring now to the drawings, where like elements are designated by like reference numerals, FIGS. 2-10B illustrate preferred systems and methods in accordance with the present invention, which can be employed to prevent the problems associated with devices currently used in the art, such as that illustrated in FIG. 1.

Figure 2:
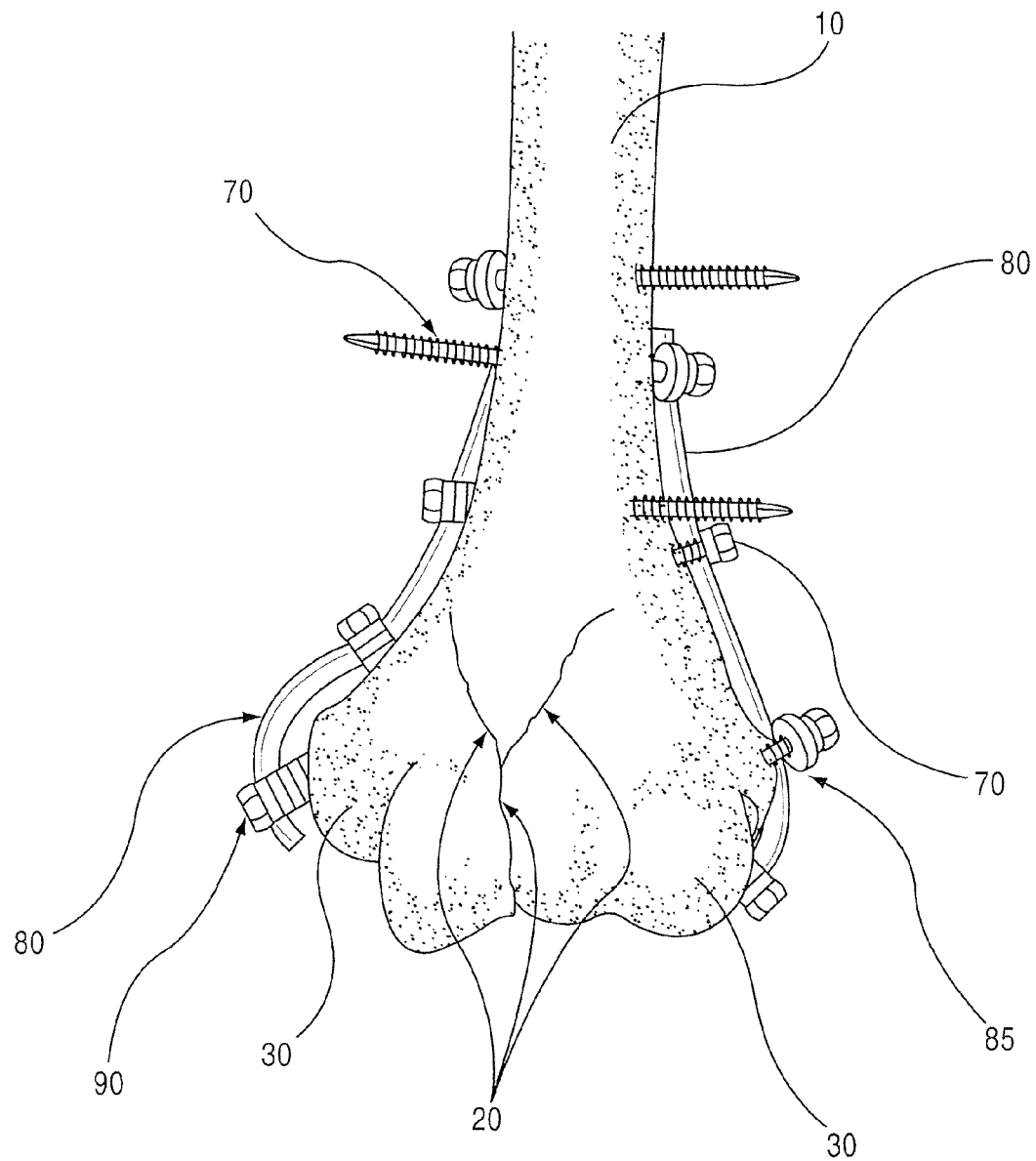
FIG. 2 is a photograph of a bone fixation system in accordance with the invention.
Figure 3:
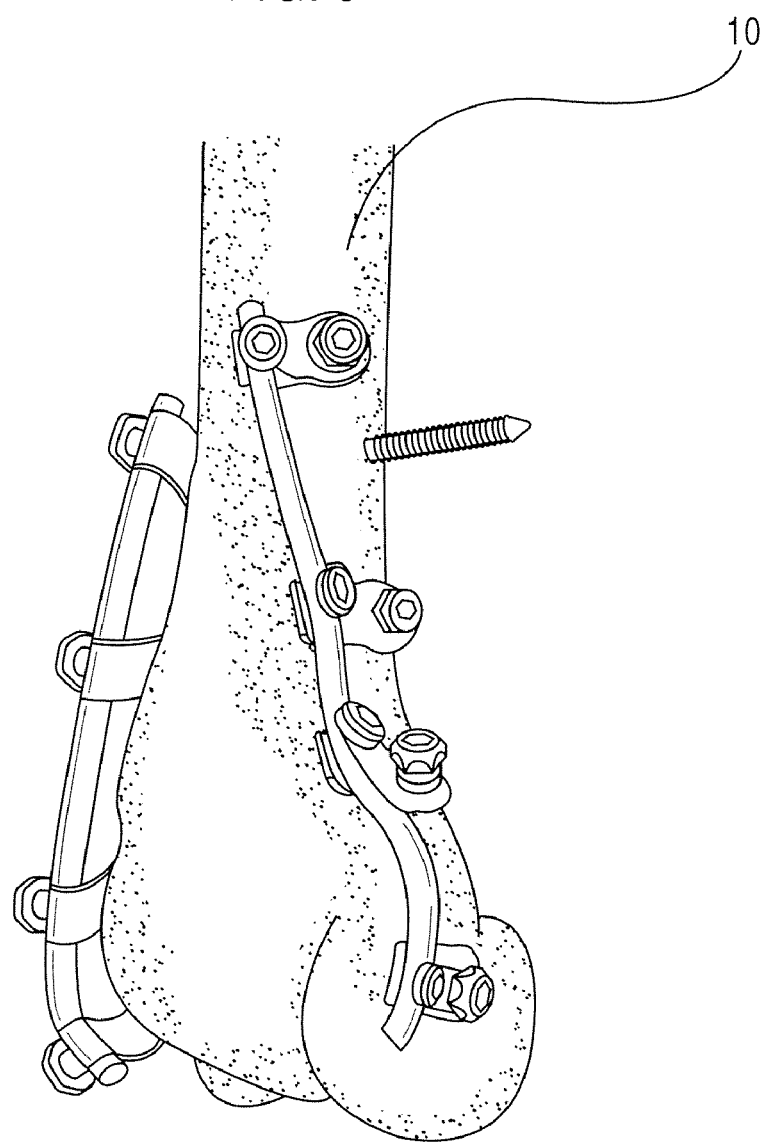
FIG. 3 is a photograph of a bone fixation system in accordance with the invention.

FIG. 2 illustrates a preferred embodiment of the present invention as it is used to achieve internal fixation of a bone fracture or fractures in the appendicular skeleton of an individual. FIG. 3 shows an alternate view of the embodiment depicted in FIG. 2.

As shown in FIG. 2, a system in accordance with the present invention is used to achieve fixation of a bone 10 having fractures 20 resulting in one or more fragments 30. The system of the present invention is applicable for use in fixating a bone or bone fragments in any mammalian individual, preferably a human. In a preferred embodiment, the system is adapted for use in the fixation of an intra-articular fracture, such as would occur, for example, in the distal humerus.

In the illustrated embodiment, the system comprises fixating screws 70 placed in the affected bone 10 in anatomically favorable positions. These fixating screws are preferably made from metal, but can comprise any material suitable for fabricating a screw adapted to be securely placed within a bone in an individual. Moreover, the fixating screws can be sized as appropriate. For example, the screws can be sized so that a minimal amount of the screw protrudes from the bone (as illustrated, for example, in FIGS. 4 and 10). The fixating screws can be placed as desired, in any position deemed appropriate for achieving maximum benefit to the individual, with at least one fixating screw 90 being placed to provide interfragmentary reduction of the bone fracture. In the present invention, the placement of the fixating screws 70,90 is not dictated or determined in any way by other components of the system. Rather, in contrast to known internal and external bone fixation devices, the fixating screws of the present invention can be placed in locations determined by one of skill in the art to be most beneficial for achieving the desired result, including, for example, the avoidance or minimization of nerve or vessel damage or excessive soft tissue stripping or injury, while achieving a strong, rigid fixation, and in many cases achieving the preservation or enhanced recovery of ranges of motion not possible with other fixation devices.

Following placement of the fixating screws 70,90, one or more rigid rods 80 is connected or attached to the fixating screws by any appropriate connecting mechanism 85. More than one rod can be used, and it is not necessary for each individual rod to simultaneously connect to each individual screw. As in the figure, each of a plurality of rods can be connected to as many screws as one of skill in the art deems appropriate to achieve a rigid fixation of the bone fracture. Once connected securely, the system holds the bone fragments in place, providing a rigid fixation, allowing the bone to repair itself and heal appropriately. Rod 80 can be fabricated from any appropriate material, but preferably comprises a metal, such as, without limitation, medical grade titanium, stainless steel, or an alloy thereof. The rod can be bent or otherwise shaped as necessary, as shown in FIGS. 2 and 3, to be adapted for connection to the fixating screws.

The rod need not be uniform in shape throughout its length, and may include a combination of rod-like portions and plate like portions. In an embodiment, the rod may, for example, have a rod-like portion that merges into a plate-like portion, wherein the rod-like portion is used where prior placement of screws is desired or critical, and the plate-like portion is used to receive screws after the rod-like portion is appropriately placed as described herein. Such a construct can be useful, for example, in a fracture involving only a distal aspect of the bone, so that proximal fixation is not dependent on the same precision in screw location or angulation as is distal fixation. Such an embodiment may offer potential advantages in cost, ease of use, and adaptability to individual fracture personality.

Figure 4:
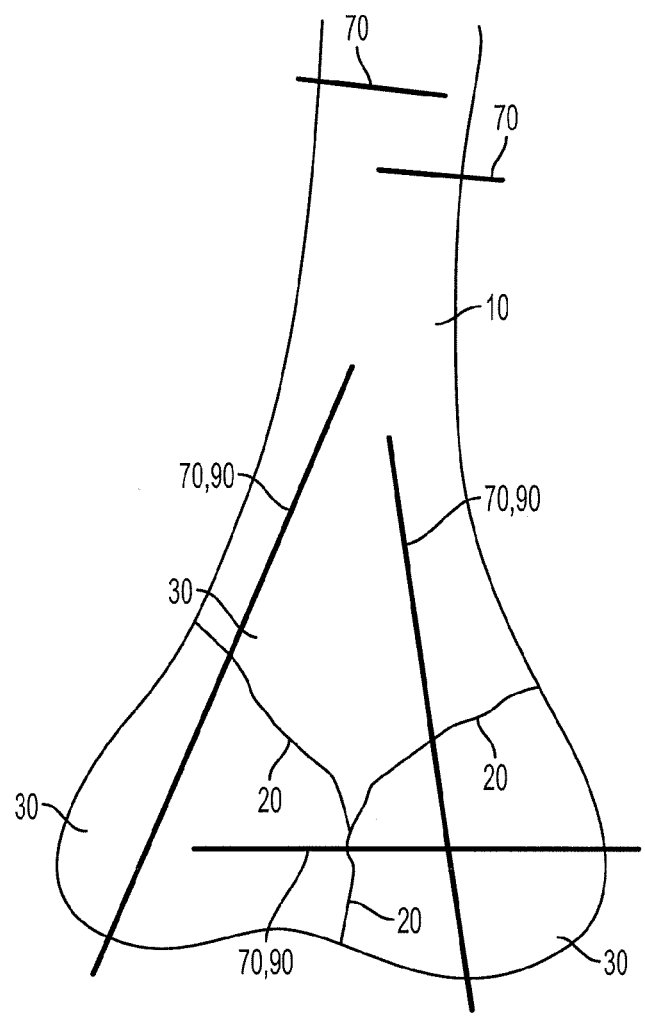
FIG. 4 is a schematic showing a bone into which fixating screws have been placed in accordance with the invention.

Referring now to FIG. 4, in a preferred method of the present invention, a plurality of fixating screws 70 is provided, each of which is placed in a bone 10 in an anatomically favorable position. The skilled artisan, such as an appropriate medical professional, has the flexibility of determining such positioning based on the individual's anatomy or other needs deemed appropriate for addressing the injury, rather than on any limitations dictated by the instrumentation at his disposal. In preferred embodiments, one or more of the screws 90 is placed in the bone to provide interfragmentary compression of a fracture or fractures 20. The method and system of the invention are particularly suited but not limited to addressing intra-articular comminuted fractures of the appendicular skeleton, which result in multiple bone fragments 30. The skilled artisan can place as many or as few fixating screws 90 as he deems appropriate to achieve optimal interfragmentary reduction of the various fragments. Moreover, he has the flexibility to place the screws in locations and at angles that are not achievable with conventional fixation devices. Once the fixating screws have been placed securely in the bone, one or more rods is connected to the fixating screws as indicated above to achieve a rigid fixation. Therefore, in methods of the present invention, bone fracture fixation is achieved using a system that provides the flexibility to determine the most favorable locations and positions of fixating screws, then securing these screws in place with one or more rigid rods.

Figure 5:
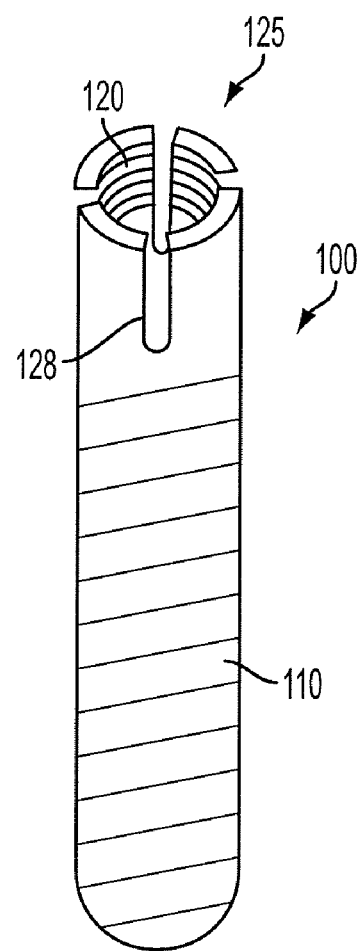
FIG. 5 depicts an exemplary fixating screw in accordance with the invention.

FIG. 5 illustrates a preferred fixating screw 100 for use in accordance with the present invention. In the illustrated embodiment, the screw comprises outer threads 110 for helping to secure it within a bone, and for helping to bring and hold bone fragments in tight cooperation when the screw is used for interfragmentary reduction of two or more fragments. The illustrated preferred fixating screw 100 also comprises an open end 125 having inner threads 120. The open end can have one or more slots or gaps 128 to allow for slight expansion of the opening's diameter upon insertion of a locking screw or other suitable locking mechanism. In a preferred embodiment, the connector for connecting the rod or rods to the fixating screws is a clamp, which can be coupled to the fixating screw and adapted to receive and secure the rod.

Figure 6:
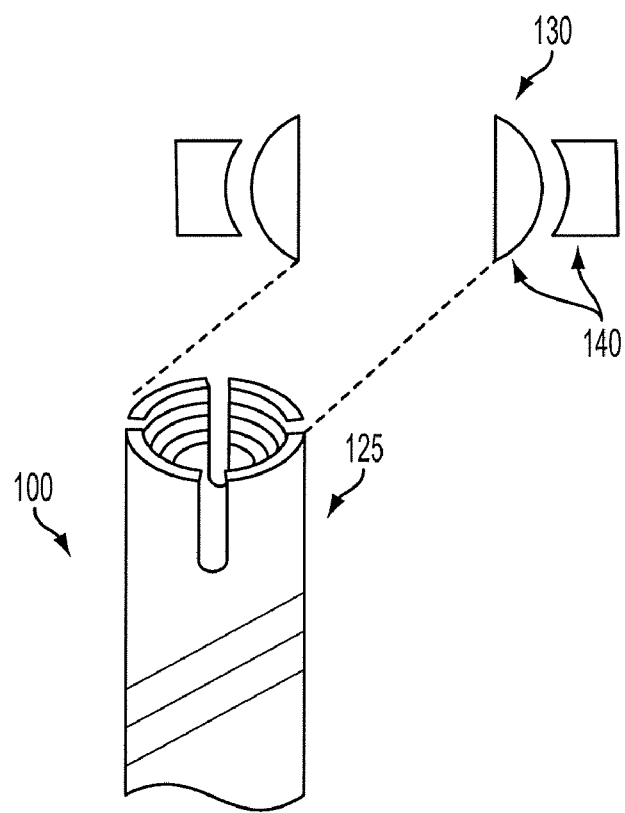
FIG. 6 illustrates placement of a clamp in relation to a fixating screw in accordance with an embodiment of the invention.

FIG. 6 illustrates an embodiment in which the clamp 130 is adapted to be placed over the open end 125 of the fixating screw 100. In this embodiment, the clamp comprises a swivel/toggle mechanism 140 which allows for an initially loose fit, later to be secured tightly once the rod is in place. This mechanism permits flexibility in the relative positions of the various components prior to final tightening.

Figure 7:
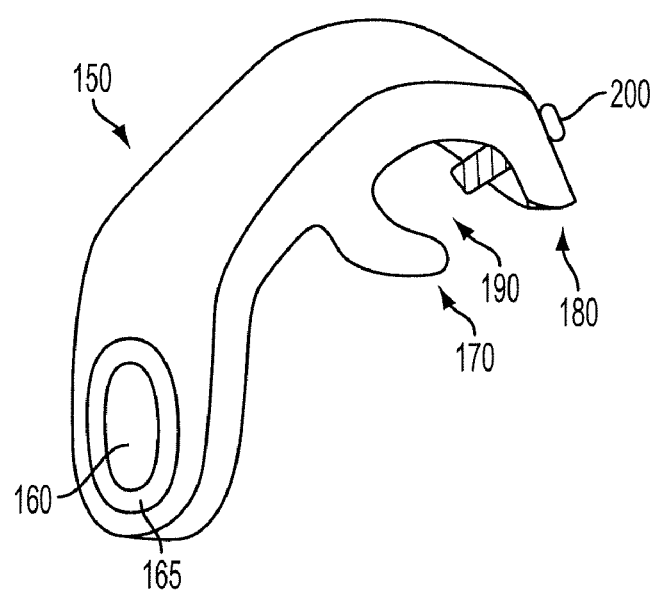
FIGS. 7-7C show exemplary clamps in accordance with embodiments of the invention.

FIG. 7 illustrates a particularly preferred embodiment of a clamp 150 for use in accordance with the invention. As shown, the clamp 150 has an opening 160 for placement over the end of a fixating screw. The illustrated embodiment includes a mechanism 165, such as the swivel/toggle mechanism described above. In the illustrated embodiment, the clamp comprises members 170, 180 that define an opening 190 through which a rod may be placed in accordance with the invention. Any suitable means can be used to secure the rod and clamp together. In the illustrated embodiment, the clamp 150 is adapted to receive a fastener screw 200 to secure the rod to the clamp.

FIG. 7A shows an alternate embodiment of a clamp 150 in accordance with the invention. In this embodiment, a rod 80 is placed in cooperation with the clamp 150.

Figure 7B:
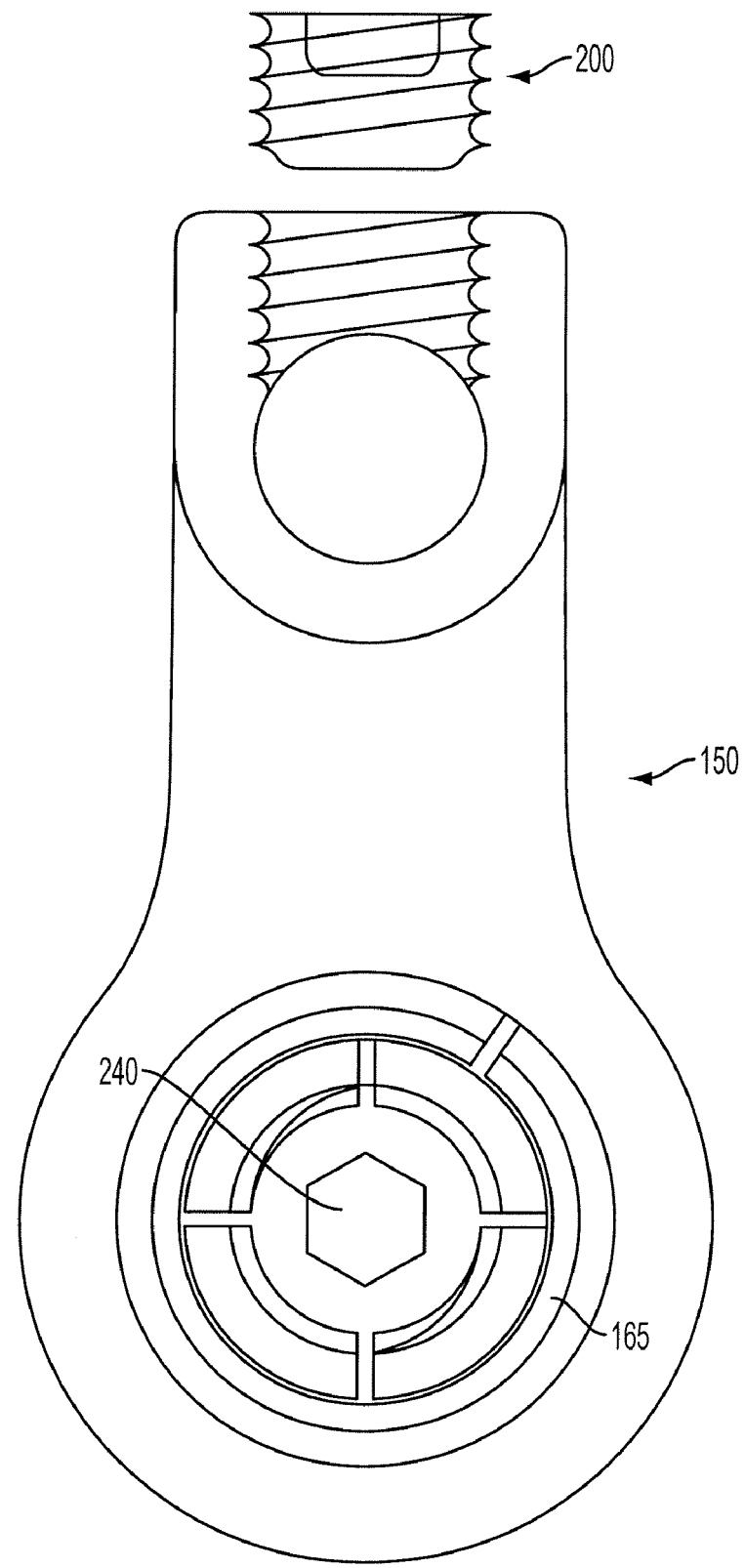

FIG. 7B illustrates an alternate view of a clamp in accordance with the invention. In this illustrated embodiment, a locking screw 240 as described herein is also shown.

Figure 7C:
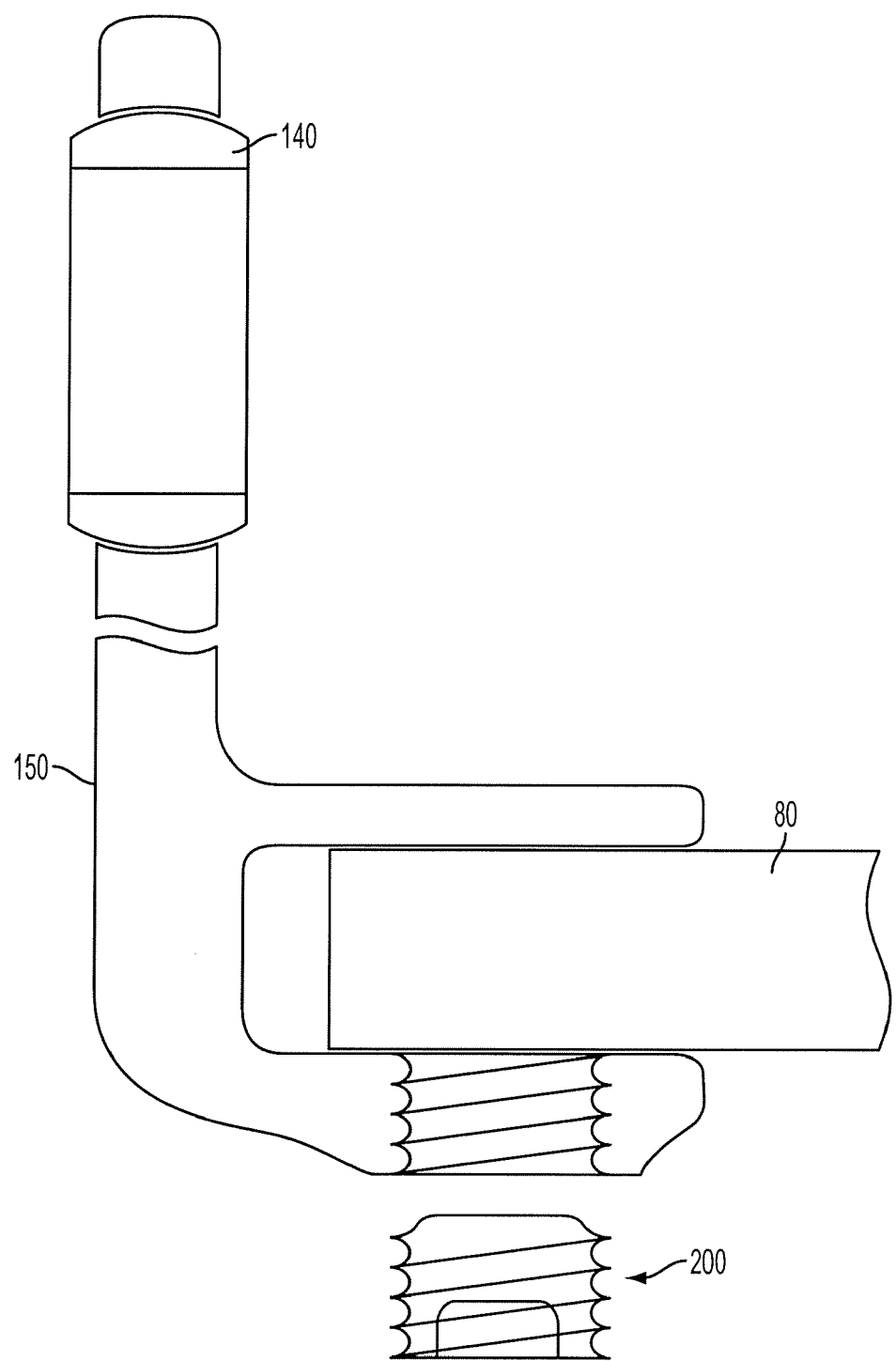

FIG. 7C illustrates another embodiment of a clamp 150 in accordance with the invention. This illustrated embodiment includes a swivel/toggle mechanism 140 as described herein.

Figure 8A:
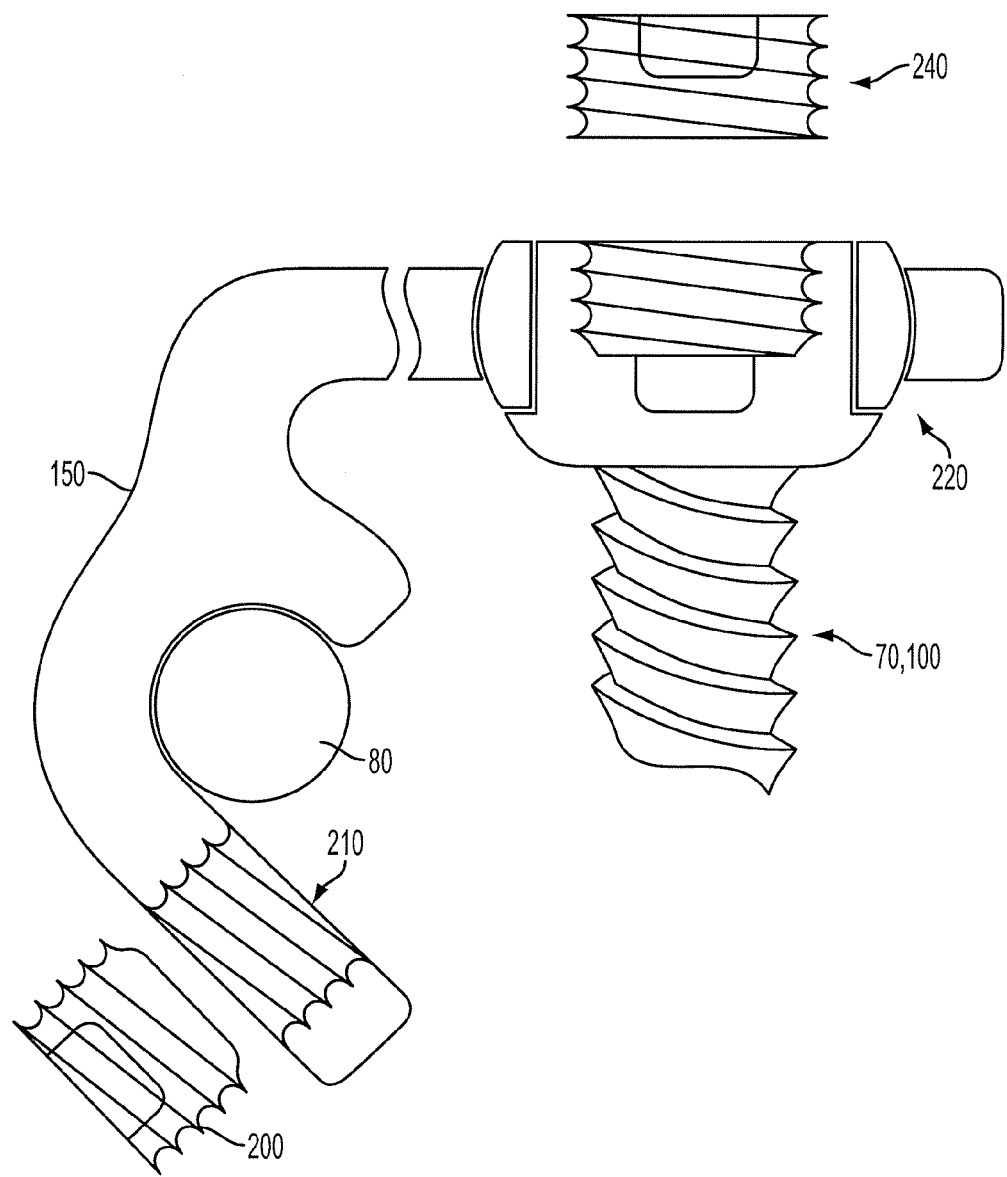

FIGS. 8 and 8A illustrate the cooperation between certain components of a system in accordance with the invention. A fixating screw 70, 100 comprising an open end 125 having slots or gaps 128 to allow for expansion, is shown in side view. A clamp 150 is also shown in side view, and is shown placed over the end of fixating screw 70, 100. As shown here, the clamp comprises a mechanism 220, such as a swivel/toggle mechanism, which allows for flexibility in achieving an initially variable positional relationship between the clamp 150 and fixating screw 70. For example, when fixating screw 70 is securely placed in a bone, the clamp 150 can be initially placed loosely over the end of the fixating screw. The mechanism 220 then allows for the clamp to be swivelled 235 or toggled 230 as necessary prior to final tightening or locking of the complete fixation system. A rod 80 is shown in cross-sectional view and is placed within opening 190 of the clamp. In the illustrated embodiment, the clamp 150 has an additional opening or hole 210 adapted to receive a fastener screw 200 to secure a rod 80 to one or more clamps. A variety of other styles and versions of clamps, fasteners, connectors, mechanisms, and securing devices can be used in accordance with the present invention to achieve the results described herein.

Figure 9:
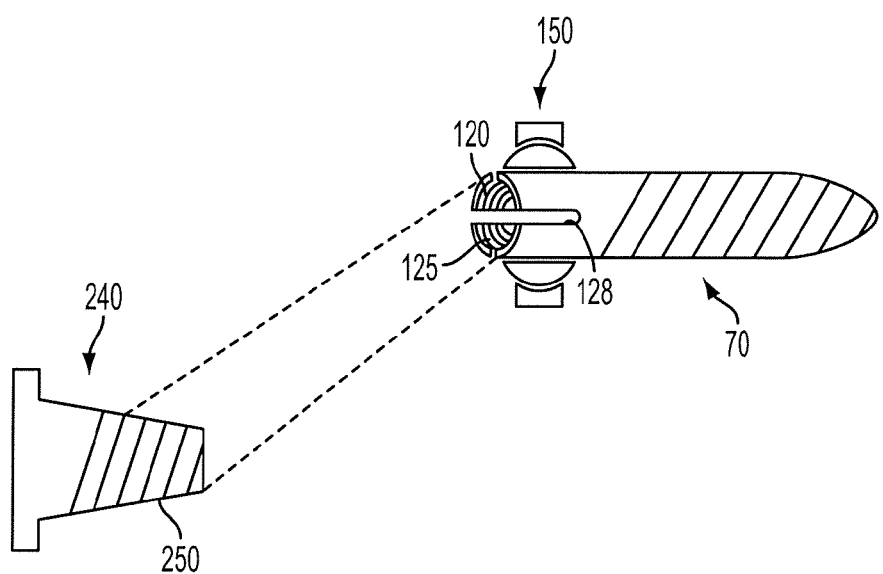
FIG. 9 illustrates placement of a tightening screw in relation to a fixating screw in accordance with an embodiment of the invention.

In the embodiment illustrated in FIG. 9, a locking screw 240 having outer threads 250 is placed within the opening 125 of the fixating screw 70 following placement of the fixating screw in a bone, placement of a clamp 150 or other suitable connector over the end of the fixating screw, and placement of a rod in secure cooperation (not shown) with the connector. In a preferred method, the outer threads 250 of the locking screw 240 engage the inner threads 120 of the fixating screw 70. Upon tightening, the slots 128 allow the opening 125 to expand, thereby securing the clamp or other connector to the fixating screw, preferably at a fixed angle. This process can be repeated with other fixating screw/connector combinations, thereby rigidly securing the entire system together to achieve a rigid fixation of the bone when the various components of the system are engaged.

FIGS. 10-10B are schematics showing preferred embodiments of the internal fixation system as it may be used in the fixation of a comminuted bone fracture. As illustrated, fixating screws 70 (and 90) are placed in a bone 10 in various desired locations and positions. The illustrated bone exhibits several fractures 20, resulting in multiple bone fragments 30. Some of the fixating screws 90 are placed in positions to achieve interfragmentary reduction of the fractures. A plurality of connectors 85 have been secured to the fixating screws, 70, 90. Two separate rods 80 are attached to the connectors to provide and maintain a strong rigid fix of the bone. One or more cross-clamps or other suitable connectors may also be employed to link together two or more rods, thereby providing increased overall system strength.

The invention further provides a fracture positioning clamp, as illustrated, for example, in FIG. 11. The fracture positioning clamp is useful while preparing the fracture for the ultimate placement of a fixation system, such as an internal system described herein. In the illustrated embodiment of the fracture positioning clamp, two "pen-type" holding devices are shown. Each such device includes a housing (1) within which is a series of components that cooperate to lock a partially threaded rod (2) in place upon application of a depressive force. The fracture positioning clamp thus serves to temporarily hold a fracture in place after reduction so that screws, such as lag screws, can be appropriately placed in an anatomically favorable position to secure the reduced fracture until a rigid fixation system can be applied. The screws may serve as the fixating screws of a fixation system described herein, or of any other appropriate fixation system that would benefit from the unique advantages provided by the fracture positioning clamp. Alternatively, additional fixating screws may be applied as appropriate, as described herein in connection with fixation systems.

In using the fracture positioning clamp of the illustrated embodiment, for example, a button mechanism (A) located on either holding device is depressed once the fracture is properly reduced or positioned. This action will lock the holding devices in position relative to each other, subject to fine adjustments, if necessary, as noted below. Prior to this locking, the holding devices each enjoy six degrees of freedom, thus allowing for a great range of motion that enables one to manipulate the fracture to insure that it is optimally reduced and placed in a position that is satisfactory to one of skill in the art prior to rigid fixation.

Upon the depression described above, the button mechanism contacts a component within the housing, such as the illustrated crown (B), that is adapted to engage the depressed button at one end and to contact a plunger (D) at the other end. Thus, upon engagement of the component (illustrated here as the crown) with the depressed button, the plunger is forced to depress and, preferably, rotate. The plunger's default position is raised or open, and can be held in such position via any suitable mechanism, such as the spring (C) shown in FIG. 11.

Any suitably-shaped or configured combination of button mechanism and component with which it engages can be used provided it achieves the desired function as described above. In alternate embodiments, for example, rather than a pen-type button and crown-shaped component configuration, a ratchet mechanism can be used to exert and maintain the depressive (and rotational) force and resulting movement and functions.

Upon depression of the button or advancement of the ratchet, the plunger engages a component that is preferably substantially spherical in shape (E). This component becomes locked between the plunger and a pad (F). The plunger is thus composed of a material that permits it to impart large frictional forces and resist motion when engaged with the substantially spherical component. This material can be any suitable material that effectively achieves or allows the result described above, but preferably includes a rubberized material or a highly beaded/roughened surface. Similarly, the substantially spherical component preferably includes a rubberized material or a metal with a highly beaded or roughened surface. The pad is preferably comprised of the same or a similar material as the plunger, i.e. a material having high frictional force characteristics. Until the substantially spherical component is engaged and locked into position, it can move freely within the housing.

In the illustrated embodiment, a sheath (H) is attached or coupled to the substantially spherical component, the sheath being adapted to accept the partially threaded rod. A distractor (J) is attachable to the sheath, and is adapted to accept the partially threaded rod and engage it at the portion of the rod bearing threads. The distractor therefore allows for small changes in length in either direction along the rod once the apparatus is locked in place. This can be accomplished, for example, by rotating the distractor in the desired direction, allowing the threads on the rod to be used in cooperation with the distractor to force the holding devices to move relatively closer or further away from each other. This configuration thus allows one to make fine adjustments even after the system is secure, when such small changes (e.g. up to a few mm) are desired to optimize the fracture reduction.

The distractor may be adapted to accept a device such as a tommy bar (I) or other suitable mechanism which is capable of increasing the moment arm and more easily imparting a rotational force.

In an embodiment, a compressor stop (K) is included within the substantially spherical component of one of the holding devices. This compressor stop is preferably a miniature plunger that serves to engage the partially threaded rod. Once the plunger mechanism is depressed, the substantially spherical component and the partially threaded rod are simultaneously engaged. The default position of the miniature plunger is in the open or raised position, which is achieved by any suitable mechanism, preferably a spring.

A female tube (G) is located at an end of each holding device. The tube is adapted to attach the device to a screw placed in the bone. This tube fits tightly over the screw allowing the holding device to impart forces through the screw and ultimately to the bone. In this manner, reduction forces can be applied by the hands of the one operating the system, through the holding devices, through the screws and to the bone. To insure that the screws yield sufficient protruding length to allow the holding device to attach, a screwdriver with a shaft that can detach from the screwdriver's handle once the screw is in place, can be utilized. In such an embodiment, the shaft remains as an extension of the fixated screw, so that the holding device can be fitted tightly over it via the female tube (G).

The locking of the components of the fracture positioning clamp in place, thus securing the fracture in the desired position, facilitates the placement of further screws, if desired, such as the fixating screws employed in connection with the internal systems described herein, so that the internal system can be utilized as described.

Thus, for example, one can utilize the fracture positioning clamp in concert with an internal fixating system as follows. When a fracture (such as in a long bone, ankle bone, or other appendicular skeletal location) has occurred for which rigid fixation is desired, screws as described above in connection with the fracture positioning clamp can be placed on either side of the fracture site. The fracture positioning clamp can then be placed on the screws as described above. Before locking the clamp, due to its allowance of a great range of motion, the fracture can be manipulated until optimal reduction and positioning is achieved. The fracture positioning clamp can then be locked, and finely adjusted if desired, as noted above. Once satisfactory fracture reduction and positioning is achieved, and the fracture positioning clamp is securely locked, one or more screws, such as lag screws, can be placed across the fracture site to stabilize the reduction. The fracture positioning clamp can then be removed and an internal fixating system as described herein can be applied. It is not necessary that the fracture positioning clamp be removed prior to applying the fixation system. Thus, fixating screws, such as those described in connection with the internal systems of the present invention, and/or the system itself, can be applied while the clamp is still in place. The clamp can then be removed following rigid fixation. Therefore, depending on whether the clamp is removed prior to application of the fixation system or not, the screws on which the holding devices had been secured, the lag screws, or any additional fixating screws can be used to secure the rod and connecting devices of the internal fixating systems described herein.

Moreover, while the fracture positioning clamp is suitable for use in concert with the internal fixation systems described herein, other suitable fixation systems and apparatus may be used following the reduction and positioning of the fracture achieved through the use of the fracture positioning clamp. Thus, the fracture positioning clamp provides a device and method for achieving an accurate and precise reduction and positioning of a bone prior to rigid fixation, that is not readily achieved through known fixation methods.

In an aspect, the invention thus provides a system and method for fixating an appendicular bone fracture in an individual, the system comprising a plurality of fixating screws, each adapted for placement in the bone at an anatomically favorable position, and at least one rigid rod attachable to the plurality of screws by a plurality of connecting devices.

The invention also provides a fracture positioning clamp comprising a plurality of holding devices each holding device comprising a substantially cylindrical housing within which is located a mechanism for imparting a direct or indirect depressional force upon a partially threaded rod. The depressional force causes each holding device to securely engage the rod, thereby locking the holding devices in position relative to each other and thereby holding the reduced fracture in place until the fracture is further secured (such as with a lag screw) and a fixation system applied.

Numerous additional applications are also within the scope of the present invention, as one of ordinary skill in the art will readily recognize. In a further embodiment, for example, the system and method can be applied to a severely comminuted fracture of the distal fibula (i.e., an ankle fracture) in a manner similar to bridge plating. In such an embodiment, the fragments and fracture bed are not disturbed, with the system being fixated both proximal and distal to the fracture location. Avoiding disruption of the fracture itself, while still maintaining length and position, avoids soft tissue stripping and loss of osteoinductive factors, such as bone morphogenetic proteins (BMP) found endogenously in fracture hematoma. The fixation system of the present invention also can be placed in a percutaneous or limited open manner, which is possible due in part to the ability to use very small screws, clamps and other connectors, with rods that are likewise themselves very narrow.

In still further embodiments, the invention is useful in, for example, forearm fractures in which rigid fixation of the radius and ulna is required. These two long bones act and articulate with one another in a manner similar to that of a joint. Typically in the art, rigid fixation of such fractures is achieved via a limited contact dynamic compression plate (LC-DCP), which allows the fracture ends to be forced together, thereby resulting in interfragmentary compression, which in turn confers significantly increased rigidity. The amount of compression in typical systems, however, is limited by the fact that the screw head itself drives the compressive force. Because a typical screw head is merely millimeters in size, it can only force the plate, and in turn, the bone, to compress a few millimeters at a time. It may be possible with present systems to then loosen one end and compress a few more millimeters with the next screw that is placed, but such a system is not optimal. The present invention overcomes this disadvantage, by allowing for an unlimited amount of compression in a single motion or step. Moreover, as described, the fixating screws can be placed in optimal anatomic position and orientation. Additionally, the time typically involved in contouring a very rigid plate to the shape of the bone can be eliminated by the use of the present system, due at least in part to the ability to use a rod with narrow width. The present system has specific usefulness in non-union, where compression and bone grafting are keys to healing.

What is claimed is:

1. A method for internal fixation of an appendicular bone fracture in an individual, said method comprising:
    providing a plurality of fixating screws;
    placing each of said fixating screws in the bone in an anatomically favorable position, wherein at least one of said fixating screws provides interfragmentary reduction of the bone fracture in lag fashion, and wherein at least one of said fixating screws comprises an open end which comprises inner threads;
    providing a plurality of clamps, each adapted for placement over the end of at least one of the fixating screws and adapted to be coupled to a rigid rod;
    placing the clamps over the ends of fixating screws;
    providing a plurality of locking screws adapted to be fitted within the open end of at least one of the fixating screws, for securing the clamps to the fixating screws;
    providing at least one rigid rod, adapted to be coupled with the clamp;
    providing a plurality of fasteners for securing the clamps to the at least one rigid rod;
    fastening the rigid rod to a plurality of clamps to provide fixation.

* * * * *